(12) United States Patent
Saito et al.

(10) Patent No.: US 7,001,894 B2
(45) Date of Patent: Feb. 21, 2006

(54) BLOOD FLOW IMPROVERS AND THROMBOSIS PREVENTIVES OR REMEDIES

(75) Inventors: Tatsuji Saito, Tokyo (JP); Koji Sakamoto, Fujioka (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/906,770

(22) Filed: Jul. 18, 2001

(65) Prior Publication Data

US 2002/0032173 A1  Mar. 14, 2002

(30) Foreign Application Priority Data

Jul. 18, 2000  (JP) ............................. 2000-217983

(51) Int. Cl.
*A01N 43/04* (2006.01)
*A61K 31/70* (2006.01)

(52) U.S. Cl. .................... 514/62; 514/54; 426/641; 426/644; 426/645; 426/658; 426/516; 426/518; 536/124; 536/127

(58) Field of Classification Search ................ 514/62, 514/54; 536/17.2, 18.7, 21, 55.2, 124, 127; 426/641, 644, 645, 658, 516, 518

See application file for complete search history.

(56) References Cited

U.S. PATENT DOCUMENTS

| | | | |
|---|---|---|---|
| 3,697,652 A | * | 10/1972 | Rovati et al. ................ 514/62 |
| 5,155,110 A | * | 10/1992 | Connor et al. .............. 514/258 |
| 5,922,692 A | * | 7/1999 | Marino ........................ 514/54 |
| 6,004,583 A | * | 12/1999 | Plate et al. .................. 424/486 |
| 6,037,333 A | | 3/2000 | Panjwani |
| 6,071,532 A | * | 6/2000 | Chaikof et al. ............. 424/450 |
| 6,171,614 B1 | * | 1/2001 | Chaikof et al. ............. 424/450 |
| 6,399,093 B1 | * | 6/2002 | Petrus ......................... 424/448 |

FOREIGN PATENT DOCUMENTS

| | | | |
|---|---|---|---|
| FR | 2473887 | * | 7/1981 |
| WO | WO 98/52576 | | 11/1998 |

OTHER PUBLICATIONS

The Merck Index, 1996, 4685.*
McCarty, Medical Hypotheses, 1997, 48, 245-251.*
The Merck Index, 1996, 4466.*
M.F. McCarty, "Glucosamine May Retard Atherogenesis by Promoting Endothelial Production of Heparan Sulfate Proteoglycans", Medical Hypotheses, (1997), 48, pp. 245-251, XP-001034746.
C.J. Meininger, et al., "Glucosamine Inhibits Inducible Nitric Oxide Synthesis", Biochemical and Biophysical Research Communications, 279, (2000), pp. 234-239, XP-001041379.
J. Schmidt, et al., "Etiology and Pathophysiology of Acute Pancreatitis", Ther Umsch, 53(5), May 1996, pp. 322-332, English Abstract Only.
V.G. Naumov, et al., "Blood Rheologic Properties in Patients with Dilated Cardiomyopathy", Bjull Vsesoiuznogo Kardiol Nauchn Tsentra AMN SSSR, 11(2), 1998, pp. 9-12, English Abstract Only.
S. Forconi, et al., "Haemorheological Disturbances and Possibility of their Correction in Cerebrovascular Diseases", J Mal Vasc, 24(2), May 1999, pp. 110-116, English Abstract Only.

* cited by examiner

*Primary Examiner*—Patrick Lewis
(74) *Attorney, Agent, or Firm*—Oblon, Spivak, McCelland, Maier & Neustadt, P.C.

(57) ABSTRACT

Glucosamine salts and derivatives are effective for the improvement of blood flow, and hence, for the prevention and/or treatment of diseases caused by blood flow disturbances, such as thrombosis. Use of glucosamine salts or glucosamine derivatives as active ingredients can provide blood flow improvers, thrombosis preventives or remedies, and dietetic drinks or foods for the improvement of blood flow or for the prevention and/or treatment of thrombosis. Administration of glucosamine salts or glucosamine derivatives can improve blood flow and can prevent and/or treat thrombosis.

7 Claims, No Drawings

BLOOD FLOW IMPROVERS AND THROMBOSIS PREVENTIVES OR REMEDIES

BACKGROUND OF THE INVENTION

Glucosamine salts, especially the sulfate or the hydrochloride have been produced, for example, by the process disclosed in JP1-28757 B or U.S. Pat. No. 3,683,076. U.S. Pat. No. 3,683,076 also discloses that glucosamine salts in the form of capsules or tablets are used as arthritis remedies. Glucosamine derivatives such as N-acetylglucosamine are also attracting increasing interests for their physiological activities.

Keeping in step with the recent westernization in diet in Japan, more and more people are suffering from diseases associated with blood flow troubles such as thrombosis. Blood flow has now come to be considered as a barometer of health. Reports on blood flow improver foods such as Japanese apricot extract are found in various sources.

SUMMARY OF THE INVENTION

With the foregoing in view, the present invention has as a primary object the provision of a novel blood flow improver which can be orally taken with ease.

The present invention relates to novel use of glucosamine salts or glucosamine derivatives based on their blood flow improving effects.

The present inventors have proceeded with screening for compounds equipped with blood flow improving effects. As a result, it has been unexpectedly found that glucosamine salts and glucosamine derivatives bring about marked improvements in blood flow when administered or otherwise taken orally, leading to the completion of the present invention.

More specifically, the present invention is concerned with blood flow improvers comprising glucosamine salts or glucosamine derivatives as active ingredients. They are useful for the prevention and/or treatment of thrombosis. They can be used as thrombosis preventives and/or remedies, or as drinks or foods for improving blood flow and preventing and/or treating thrombosis. Specifically, the present invention provides the following improver, preventive or remedy, dietetic drink or food, methods and use:

(1) A blood flow improver comprising a glucosamine salt or a glucosamine derivative as an active ingredient.
(2) A thrombosis preventive or remedy comprising a glucosamine salt or a glucosamine derivative as an active ingredient.
(3) A dietetic drink or food for the improvement of blood flow or for the prevention or treatment of thrombosis, comprising a glucosamine salt or a glucosamine derivative.
(4) A method for improving blood flow, which comprises administering an effective amount of a glucosamine salt or a glucosamine derivative to a human being.
(5) A method for preventing or treating thrombosis, which comprises administering an effective amount of a glucosamine salt or a glucosamine derivative to a patient.
(6) Use of a glucosamine salt or a glucosamine derivative for the improvement of blood flow through a human being.
(7) Use of a glucosamine salt or a glucosamine derivative for the prevention or treatment of human thrombosis.

A marked improvement or increase in blood flow can be observed in a short time after administration of a glucosamine salt or derivative. The present invention is, therefore, effective for the maintenance of health and also for the prevention and/or treatment of thrombosis.

DETAILED DESCRIPTION OF THE INVENTION AND PREFERRED EMBODIMENTS

The present invention will hereinafter be described in more detail.

No particular limitation is imposed on the glucosamine salt for use in the present invention insofar as it is pharmaceutically acceptable. Inorganic acid salts and organic acid salts are both usable. In general, however, inorganic acid salts such as the sulfate and the hydrochloride are employed, with the hydrochloride being preferred in the present invention. Examples of organic acid salts usable in the present invention can include the acetate, the citrate and the malate.

Illustrative of the glucosamine derivative are those obtained individually by modifying the amino group of glucosamine with a low molecular weight group, for example, a group the molecular weight of which is in a range of from 15 to 150, such as an alkyl group or an acyl group.

Although it has not been elucidated through what mechanism a glucosamine salt or derivative can achieve blood flow improving effects, the glucosamine salt or derivative is known to be metabolized subsequent to its conversion into free glucosamine in the living body. Accordingly, one readily convertible into glucosamine as a result of removal of the modifying group by an acid or a bioenzyme, such as a glucosamine salt or N-acylglucosamine or a salt thereof, is considered to be preferable. Preferred examples of glucosamine derivatives can, therefore, include those obtained by protecting the amino group of glucosamine with groups such as lower acyl, lower sulfonyl or lower phosphonyl groups, respectively, for example, N-(lower acyl)glucosamines, N-(lower sulfonyl)glucosamines or N-(lower phosphonyl)glucosamines.

Illustrative of the lower acyl group in the present invention can include $C_{1-6}$ acyl groups, with $C_{1-3}$ acyl groups being preferred.

The blood flow improver and the thrombosis preventive or remedy according to the present invention may consist of the glucosamine salt or derivative alone, but generally, can be provided by formulating a glucosamine salt with drug, drink or food additives such as a carrier, an excipient and auxiliaries (a corrigent, a sweetener, a binder, etc.) into a liquid or solid preparation such as a drink, a tablet, a granule, a powder, a capsule or a jelly by a method known per se in the art. Examples of the carrier and excipient can include water and saccharides. The content of the glucosamine salt or derivative in the improver, preventive or remedy may be, but is not limited to, generally 0.2% (by weight; this will hereinafter apply equally) or more, preferably 1% or more, and may range up to 100%.

The dietetic drink or food according to the present invention for the improvement of blood flow or for the prevention or treatment of thrombosis can be obtained by mixing the glucosamine salt or derivative with an adequate drink or food.

No particular limitation is imposed on the drink or food with which the glucosamine salt or derivative can be mixed. Illustrative of the drink or food are milk drinks such as milk, beverages such as health promoting drinks, and foods such as ham and sausages.

The content of the glucosamine salt or derivative in the dietetic drink or food is not limited specifically, and may be generally 0.1% or more, preferably 0.3% or more, more preferably 0.5% or more, all based on the amount of the whole drink or food. No particular limitation is imposed on the upper limit of the content, but from the standpoint of taste and the like, the upper limit may be generally 10%, preferably 5%, more preferably 4%.

The method according to the present invention for improving blood flow can be carried out by administering to a patient an effective amount of the glucosamine salt or derivative either alone or together with one or more non-toxic additives, which may include the above-described drink or food, optionally after formulating the glucosamine salt or derivative and the one or more non-toxic additives into a blood flow improver or a thrombosis preventive or remedy.

The daily dose per adult of the glucosamine salt or derivative as the blood flow improver or the thrombosis preventive or remedy may be, but is not limited to, generally 0.3 g or more, preferably 0.5 g or more, more preferably 1 g or more. No particular limitation is imposed on the upper limit as the glucosamine salt or derivative is practically free of toxicity, but the upper limit may be generally 20 g, preferably 10 g, more preferably 5 g.

The present invention will hereinafter be described based on the following Tests and Examples.

Test 1

From each of adult volunteers (A: male, B: female, C: female, D: female, E: male) who had taken usual breakfast, a first blood sample (10 mL) was collected at 1:00 p.m. Immediately after the collection of the blood sample, 1.5 g of glucosamine hydrochloride with 50 mL of water was administered to the volunteer. Blood samples (10 mL, each; 5% heparinated) were collected upon elapsed time of 30 min, 60 min and 90 min after the administration. The fluidity of each blood sample was determined by a microchannel array flow analyzer (MC-FAN) which is a capillary model fabricated by VLSI technology. The determination was carried out as will be described below.

Determination of Blood Flow Improving Effects

A fresh 5%-heparinated whole blood sample, which had been obtained by adding 0.5 part by weight of a 1,000 IU/mL heparin sodium solution to 9.5 parts by weight of the corresponding blood sample, was caused to flow through an array of 8,736 parallel microchannels of 7 μm in width, 30 μm in length and 4.5 μm in depth (Bloody 6–7) under 20 cmH$_2$O suction by using the microchannel array flow analyzer (MC-FAN). A transit time necessary for 100 μL of the whole blood sample to pass through the microchannels was measured. Using a transit time necessary for 100 μL of physiological saline to pass through the microchannels as measured just before the blood measurement, the transit time of the whole blood sample was converted in accordance with the following equation:

Transit time of the whole blood× 12 sec/transit time of the physiological saline to obtain a value which would have been available if the transmit time of physiological saline had been 12 sec. The value was recorded as a blood transit time.

The results are shown in Table 1, including indices of whole blood transit times of the blood samples collected after the administration of the glucosamine hydrochloride based on those of the corresponding blood samples collected before the administration of glucosamine hydrochloride (% relative to an initial value of 100%).

TABLE 1

Changes in Blood Transit Time

| Volunteer* | Transit time (sec) | | | |
|---|---|---|---|---|
| | 0 | 30 min | 60 min | 90 min |
| A | 46.1 | 36.1 | 37.1 | — |
| B | 32.9 | 28.6 | 27.4 | — |
| C | 47.0 | 38.6 | 42.3 | — |
| D | 78.0 | 37.1 | 33.2 | — |
| E | 47.3 | 35.3 | 28.7 | 31.6 |
| Mean | 50.3 | 35.1 | 33.7 | — |
| ±SD | 16.6 | 3.9 | 6.1 | — |
| ±SE | 4.1 | 2.0 | 2.5 | — |
| Index (%) | 100 | 70.0 | 67.1 | — |

*Time elapsed after administration (min)

As is evident from Table 1, the transit times of the whole blood samples (100 μL) collected after the administration of glucosamine hydrochloride decreased to 60.7% to 74.6% of the corresponding transit times before the administration, thereby demonstrating the availability of marked blood flow improving effects by the administration of a glucosamine salt.

EXAMPLE 1

The following ingredients were dissolved in distilled water to give a glucosamine-salt-containing, blood flow improver drink (pH 2.35) as much as 50 mL in total volume.

| Ingredient | |
|---|---|
| Erythritol | 5 g |
| Trehalose | 1 g |
| Glucosamine hydrochloride | 1.5 g |
| Cyclic oligosaccharide | 1.5 g |
| Vitamins B1, B2, B6 | 17 mg |
| Sour agent | q.v. |
| Flavor | trace |

Test 2

From each of male/female adult volunteers (A: male, B: male, C: male, D: female), a first blood sample (10 mL) was collected in a similar manner as in Test 1. Immediately after the collection of the blood sample, 50 mL of the glucosamine-salt-containing, blood flow improver drink was administered to the volunteer. Following the procedure of Test 1, blood samples (10 mL, each; 5% heparinated) were collected upon elapsed time of 30 min, 60 min and 90 min after the administration. The fluidity of each blood sample was determined in a similar manner as in Test 1. The results are shown in Table 2.

TABLE 2

Changes in Blood Transit Time

| Volunteer* | Transit time (sec) | | | |
|---|---|---|---|---|
| | 0 | 30 min | 60 min | 90 min |
| A | 42.1 | 24.5 | 26.2 | 29.2 |
| B | 41.7 | 32.9 | 33.2 | 31.1 |
| C | 33.4 | 27.0 | 23.8 | 23.1 |
| D | 45.9 | 34.0 | 41.9 | 23.7 |
| Mean | 40.8 | 29.6 | 31.3 | 26.8 |

TABLE 2-continued

Changes in Blood Transit Time

| Volunteer* | Transit time (sec) | | | |
|---|---|---|---|---|
| | 0 | 30 min | 60 min | 90 min |
| ±SD | 5.3 | 4.6 | 8.1 | 4.0 |
| ±SE | 2.7 | 2.3 | 4.1 | 2.0 |
| Index (%) | 100 | 72.5 | 76.7 | 65.7 |

*Time elapsed after administration (min)

Test 3

A test was carried out as in Test 1 except that N-acetylglucosamine was used instead of glucosamine hydrochloride, and blood flow improving effects of N-acetylglucosamine were determined in a similar manner as in Test 1.

The mean blood transit time was 60.9 sec before the administration. Upon elapsed time of 30 min after the administration, the mean blood transmit time significantly decreased to 36.5 sec. Upon elapsed time of 1 hr after the administration, the mean blood transit time increased back to the value before the administration.

The invention claimed is:

1. A method for treating thrombosis, which comprises administering to a patient in need thereof an effective amount of a glucosamine salt; wherein said salt is an organic salt.

2. The method of claim 1, wherein said administering is orally.

3. The method of claim 1, wherein said glucosamine salt is contained in a dietetic drink or food.

4. The method of claim 1, wherein said organic salt is selected from the group consisting of acetate, citrate, and malate.

5. The method of claim 1, wherein said effective amount is a daily dose for an adult of 0.3 grams or more.

6. The method of claim 5, wherein said effective amount is a daily dose for an adult of less than 20 grams.

7. The method of claim 1, wherein said effective amount is a daily dose for an adult of less than 20 grams.

* * * * *